(12) United States Patent
'T Hooft et al.

(10) Patent No.: US 10,363,101 B2
(45) Date of Patent: Jul. 30, 2019

(54) OPTICAL SHAPE SENSING SYSTEM, MEDICAL APPARATUS AND METHOD FOR OPTICAL SHAPE SENSING

(71) Applicant: KONINKLIJKE PHILIPS N.V., Eindhoven (NL)

(72) Inventors: Gert Wim 'T Hooft, Eindhoven (NL); Theodorus Thomas Marinus van Schaijk, Eindhoven (NL); Jeroen Jan Lambertus Horikx, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/539,376

(22) PCT Filed: Jan. 4, 2016

(86) PCT No.: PCT/EP2016/050031
§ 371 (c)(1),
(2) Date: Jun. 23, 2017

(87) PCT Pub. No.: WO2016/110467
PCT Pub. Date: Jul. 14, 2016

(65) Prior Publication Data
US 2018/0263709 A1    Sep. 20, 2018

(30) Foreign Application Priority Data

Jan. 8, 2015 (EP) .................................... 15150403

(51) Int. Cl.
*G01L 1/24* (2006.01)
*A61B 34/20* (2016.01)
*G01B 11/16* (2006.01)

(52) U.S. Cl.
CPC ............ *A61B 34/20* (2016.02); *G01B 11/161* (2013.01); *G01B 11/18* (2013.01); *G01L 1/246* (2013.01); *A61B 2034/2061* (2016.02)

(58) Field of Classification Search
CPC ............ A61B 34/20; A61B 2034/2061; B01B 11/161; B01B 11/18; G01L 11/246
See application file for complete search history.

(56) References Cited

U.S. PATENT DOCUMENTS 7,042,573 B2 * 5/2006 Froggatt ............ G01M 11/3181
                                                          356/479
7,330,245 B2    2/2008 Froggatt
(Continued)

FOREIGN PATENT DOCUMENTS

CN         104034257 A  *  9/2014

*Primary Examiner* — Dominic J Bologna (57) ABSTRACT

The present invention relates to an optical shape sensing system for sensing a shape of a medical device (24), comprising an input polarization controller (12) for setting an input polarization state of an input light signal, at least one interferometer unit (18) for dividing said polarized input light signal into a device signal and a reference signal, guiding said device signal to be scattered within an optical fiber (19) inserted into said device (24) and coupling said scattered device signal with said reference signal to form an output light signal, and at least one measurement branch (39) comprising an output polarization controller arrangement (26) for setting an output polarization state of said output light signal, a polarizing beam splitter (30) for splitting said polarized output light signal into two signal portions, each being in a corresponding one of two signal portion polarization states, and a detector arrangement (35) comprising two detectors (32, 34), each for detecting a corresponding one of said two signal portions, wherein said input polarization controller (12) is configured to set two pairs of input polarization states, or said output polarization controller
(Continued)

arrangement (26) is configured to set two output polarization states each for enabling a corresponding one of two pairs of signal portion polarization states, wherein each pair of input or signal portion polarization states are representable by a corresponding one of two axes in a Poincaré sphere different from each other.

14 Claims, 5 Drawing Sheets

(56) References Cited

U.S. PATENT DOCUMENTS

| | | | |
|---|---|---|---|
| 7,379,168 B2 | 5/2008 | Froggatt et al. | |
| 7,538,883 B2 | 5/2009 | Froggatt | |
| 8,773,650 B2 | 7/2014 | Froggatt et al. | |
| 9,553,664 B2 | 1/2017 | Horikx et al. | |
| 2010/0141930 A1 | 6/2010 | Omichi et al. | |
| 2011/0090486 A1 | 4/2011 | Udd | |
| 2011/0109898 A1* | 5/2011 | Froggatt | G01B 11/18 356/73.1 |
| 2011/0144505 A1* | 6/2011 | Yamamoto | A61B 5/0064 600/476 |
| 2011/0255077 A1* | 10/2011 | Rogers | G01L 1/242 356/73.1 |
| 2012/0038885 A1* | 2/2012 | Cense | A61B 3/102 351/206 |

* cited by examiner

OPTICAL SHAPE SENSING SYSTEM, MEDICAL APPARATUS AND METHOD FOR OPTICAL SHAPE SENSING

CROSS-REFERENCE TO PRIOR APPLICATIONS

This application is the U.S. National Phase application under 35 U.S.C. § 371 of International Application Serial No. PCT/EP2016/050031, filed on Jan. 4, 2016, which claims the benefit of European Patent Application No. 15150403.2, filed on Jan. 8, 2015. These applications are hereby incorporated by reference herein.

FIELD OF THE INVENTION

The present invention relates to an optical shape sensing system, a medical apparatus and a method for performing optical shape sensing. It finds application in elongated medical devices such as endoscopes, catheters and guidewires used in the area of image guided interventions and therapy.

BACKGROUND OF THE INVENTION

Optical shape sensing (OSS) is an optical measurement technique for determining the position and shape of a structure in a three dimensional space. In particular, optical shape sensing can be applied for minimally invasive procedures in health care, wherein it is advantageous to monitor the three dimensional shape of an elongated medical device, e.g. endoscopes, catheters or guidewires, with minimal use of harmful radiation.

To this end, an optical shape sensing technology is developed based on back scatter reflectometry. The light of a light source is split into a reference signal and a device signal, wherein both signals are guided in fibers through an interferometer. The device signal is guided first to undergo scatterings within the fiber portion that is inserted into a medical device and subsequently to interfere with the reference signal due to their different optical paths. Based on the interference signal, information regarding mechanical strains due to shape deformations of the device can be retrieved.

Shape deformations not only give rise to length variations of the medical device but also to changes in the refractive index. Moreover, such changes are usually not isotropic, but depend on the polarization of the impinging light. For instance, the impinging light polarized parallel to the direction of curvature has a different refraction index from the impinging light polarized perpendicularly to the direction of curvature.

This phenomenon is known as birefringence, which has two effects for the optical shape sensing. First of all, it changes the state of polarization of the scattered, in particular reflected signal dependent on the position of the scattering point within the device. In particular, the total optical path from the laser source to the scattering point and subsequently towards the detector is dependent on the actual position of the scattering point. For a given polarization of the input light the detected light from some of the scattering points may have a state of polarization that is orthogonal to the state of polarization of the reference signal. This leads to polarization fading, due to which no information can be retrieved for such scattering points.

In addition, a change in the refraction index cannot be disentangled or decoupled from a mechanical length change and will influence the phase of the interference signal. Consequently, the result of the strength measurement as well as the optical shaped sensing will be no longer reliable. Moreover, due to the non-isotropic nature of birefringence, the interference signal will depend on the exact state of polarization set for the laser source and possibly also on the exact state of polarization of the detector arrangement.

U.S. Pat. No. 8,773,650 B2 discloses an accurate measurement method and an apparatus for shape sensing with a multi-core fiber. A change in optical length is detected in one of the cores in a multi-core fiber up to a point on the multi-core fiber. A location and/or pointing direction are/is determined at the point on the multi-core fiber based on the detected changes in optical length. The accuracy of the determination is better than 0.5% of the optical length of the multi-core fiber up to the point on the multi-core fiber. In an example embodiment, the determining includes determining a shape of at least a portion of the multi-core fiber based on the detected changes in optical length.

EP 2 720 388 A1 discloses an optical frequency domain reflectometry system comprising a first coupling point arranged for a splitting radiation into two parts, so that radiation may be emitted into a reference path and a measurement path. The system further comprises an optical detection unit capable of obtaining a signal from the combined optical radiation from the reference path and the measurement path via a second coupling point. The measurement path comprises a polarization dependent optical path length shifter, which may create a first polarization and a second polarization in the measurement path, where the optical path length is different for the first and second polarizations in the measurement path.

WO 2010/073002 A1 discloses a distributed optical fiber sensor which uses a sensor fiber having a low or zero intrinsic birefringence that is responsive to an environmental parameter such as pressure. Probe light pulses having a diversity of launched polarization states are used to reduce signal fading and polarization dependent loss in the retardation speed frequency signals which are sensed and then analyzed to determine the environmental parameter as a profile along the sensor fiber.

SUMMARY OF THE INVENTION

It is an object of the present invention to provide an optical shape sensing system, medical apparatus and method for optical sensing which enable counteracting polarization fading due to birefringence and improved control of the polarization state of light.

In a first aspect of the present invention an optical shape sensing system for sensing a shape of a medical device is presented that comprises an input polarization controller for setting an input polarization state of an input light signal, at least one interferometer unit for dividing the polarized input light signal into a device signal and a reference signal, guiding said device signal to be scattered within an optical fiber inserted into the device and coupling said scattered device signal with the reference signal to form an output light signal, and at least one measurement branch comprising an output polarization controller arrangement for setting an output polarization state of the output light signal, a polarizing beam splitter for splitting the polarized output light signal into two signal portions, each being in a corresponding one of two signal portion polarization states, and a detector arrangement comprising two detectors, each for detecting a corresponding one of the two signal portions, wherein the input polarization controller is configured to set two pairs of input polarization states, and/or the output polarization controller arrangement is configured to set two output polarization states each for enabling a corresponding one of two pairs of signal portion polarization states, wherein each pair of input and/or signal portion polarization states are representable by a corresponding one of two axes in a Poincaré sphere different from each other.

In a further aspect of the present invention a medical apparatus for optical shape sensing is presented that comprises a medical device and an optical shape sensing system as claimed herein for sensing a shape of the medical device.

In a further aspect of the present invention a method for optical shape sensing is presented which comprises the steps of setting an input polarization state of an input light signal, dividing the polarized input light signal into a device signal and a reference signal, guiding the device signal to be scattered within an optical fiber inserted into the device and coupling the scattered device signal with the reference signal to form an output light signal, setting an output polarization state of the output light signal, splitting the polarized output light signal into two signal portions, each being in a corresponding one of two signal portion polarization states, and detecting the two signal portions, wherein the setting comprises setting two pairs of input polarization states, and/or two output polarization states each for enabling a corresponding one of two pairs of signal portion polarization states, wherein each pair of input and/or signal portion polarization states are representable by a corresponding one of two axes in a Poincaré sphere different from each other.

Preferred embodiments of the invention are defined in the dependent claims. It shall be understood that the claimed apparatus and method have similar and/or identical preferred embodiments as the claimed system and as defined in the dependent claims.

The input light signal is generated by a light source, for instance a tunable laser source (TLS), which preferably is a part of the optical shape sensing system. The input light signal is preferably polarized upon generation. The input polarization controller sets the polarization state of the input light signal to be the input polarization state. After being divided into the device signal and the reference signal, the device signal is guided by the optical fiber, which has a fiber sensor portion inserted into the device. The optical fiber is preferably a part of the optical shape sensing system and comprises at least one core. The device signal undergoes a scattering, in particular a reflection within the fiber sensor portion of the optical fiber. The reference signal is guided through the reference branch directly to be coupled with the scattered device signal. The two signals interfere with each other into an output light signal.

The output light signal is further processed for measurement in the measurement branch. The output polarization controller arrangement comprises at least one output polarization controller that sets the polarization state of the output light signal to be the output polarization state. The polarizing beam splitter splits the polarized output light signal into the two signal portions which are separately detected by a corresponding detector.

Advantageously, the present optical shape sensing system overcomes signal degradation due to polarization fading. Also, it enables to account for different polarization variations in multi-core optical fibers. For instance, the optical fiber may comprise four cores, each guiding its own device signal interrogated simultaneously with its own interferometer.

Furthermore, the present invention also enables to analyze the interference signals in such a way that the result of the analysis is not dependent on the input and/or output polarization state, i.e. the setting of the input and/or output polarization controller.

In addition, the present invention advantageously increases the signal to noise ratio (SNR) of the detected light signals. The sensitivity of optical shape sensing to birefringence is reduced, leading to increased accuracy of the sensing results and improved birefringence correction.

The optical shape sensing system is configured to carry out optical shape sensing using two schemes. In the first scheme, two pairs of input polarization states can be set by the input polarization controller. In the second scheme, two pairs of signal portion polarization states can be set using the output polarization controller arrangement assisted by the polarizing beam splitter. The detector arrangement can be set to detect the signal portions.

Each pair of the input or signal portion polarization states are representable by a corresponding one of two axes in a Poincaré sphere that are sufficiently different from each other. In particular, the two axes of the Poincaré sphere do not overlap with each other, wherein they are not parallel to each, either. In this way, at least two axes in the Poincaré sphere can be probed for optical shape sensing by properly setting the input and/or the output polarization controller. In addition to increased number of measurement configurations and consequently reduced error, the present invention advantageously enables a polarization diversity measurement with improved birefringence correction.

Preferably, each pair of input polarization states in the first scheme are set in combination with one pair of signal portion polarization states. Further preferably, each pair of signal portion polarization states in the second scheme are set in combination with one pair of input polarization states. In both schemes, three axes of the Poincaré sphere can be probed. In the first scheme, two axes represent the two pairs of input polarization states while a third axis represents the pair of signal portion polarization states. In the second scheme, two axes represent the two pairs of signal portion polarization states while a third axis represents the pair of input polarization states. Preferably, the three axes are perpendicular to each other.

In a preferable embodiment, each pair of input or signal portion polarization states are representable by a corresponding one of two axes in a Poincaré sphere perpendicular to each other. In this way, at least two axes in the Poincaré sphere which are perpendicular to each other can be probed for optical shape sensing by properly setting the input and/or the output polarization controller. The present invention advantageously enables a polarization diversity measurement with further improved birefringence correction.

In another preferable embodiment, the two signal portion polarization states are orthogonal to each other. The measurement branch thus enables two pairs of orthogonal signal portion polarization states. Advantageously, the anisotropy properties of birefringence can be investigated in this way so that the birefringence correction can be further improved.

In another preferable embodiment, each of the two pairs of input polarization states comprises two input polarization states orthogonal to each other. The input polarization controller thus enables two pairs of orthogonal input polarization states. Advantageously, the anisotropy properties of birefringence can be investigated in more details in this way so that the birefringence correction can be further improved.

In another preferable embodiment, the output light signal comprises two separate output signal parts, the output polarization controller arrangement being configured to set for each of the output signal parts a corresponding one of the two output polarization states. In this way, each output signal part is polarized to a corresponding output polarization state. Different axes in the Poincaré sphere can be separately probed, which has the advantage of reduced measurement error.

In another preferable embodiment, the output polarization controller arrangement comprises two polarization controllers, each for setting one of the two output polarization states. The two output signal parts can be set to their corresponding output polarization state simultaneously. This advantageously reduces the measurement duration for probing two axes in the Poincaré sphere. In another preferable embodiment, two polarization beam splitters and/or two detector arrangements are provided each for a corresponding one of the two output signal parts. In this way, the two pairs of signal portion polarization states can be simultaneously generated, and/or detected using different pairs of detectors. Advantageously, this further reduces the measurement duration for birefringence correction.

In another preferable embodiment, each pair of the signal portion polarization states are representable by two points on a surface of the Poincaré sphere defining a corresponding one of the two perpendicular axes of the Poincaré sphere. In this way, two axes traversing the origin of the Poincaré sphere can be probed in the optical shape sensing. Advantageously, the optical shape sensing system is able to perform a polarization diversity measurement with further improved birefringence correction.

In another preferable embodiment, the two signal portions have equal signal amounts or one of the two signal portions has a signal amount essentially equal to zero. In this way, the present invention enables different output polarization states, in which the polarized output light signal is projectable to only one detector or both detectors with equal signal amounts. Advantageously, this increases the sensitivity of the polarization diversity measurement, so that the birefringence correction is more accurate. When the laser light is tuned in wavelength, the interference signal will give rise to high frequency modulation on the detector. The light from the reference branch alone will give a DC signal. By separating DC from AC calibration or DC balancing can be performed.

In another preferable embodiment, the interferometer unit comprises a polarization controller for setting a polarization state of the device signal, the polarization controller being arranged on an upstream signal side of the device. In this way, the device signal can be set to a polarization state independently from the reference signal. Advantageously, this enables to adjust the polarization state of the device signal separately.

In another preferable embodiment, the input polarization controller is configured to set a reference polarization state of the reference signal, wherein the reference polarization state corresponds to an eigen polarization mode of an optical fiber guiding the reference signal. In this way, an optimal setting for the input polarization controller can be determined with short duration. Advantageously, the efficiency and reliability of birefringence correction is improved.

In another preferable embodiment, the optical shape sensing system further comprises the optical fiber, the optical fiber comprising at least one, preferably at least four cores each for separately guiding a corresponding one of at least four device signal parts of the device signal, and further comprising at least one, preferably at least four interferometer units, wherein each core of said optical fiber is configured to cooperate with a corresponding interferometer unit and/or measurement branch When the fiber contains multiple cores, preferably four cores, one needs to have the same amount of interferometers. Preferably, the interferometers cooperate with the same set of light source and input polarization controller. Before entering the interferometers, the light signal needs to be split in four parts for the four interferometers. The fiber is preferably connected to a so-called fanout that assembles/divides the signals from four single core fibers into one multi-core fiber. The four cores are advantageous for measuring axial strain occurring for instance due to temperature variations, bending in horizontal plane, bending in vertical plane and twist or axial rotation. The four cores each have their own polarization diversity scheme.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

In optical shape sensing technology based on backscatter reflectometry, light generated by a light source is divided into a device signal and a reference signal. The device signal is guided in an optical fiber comprising a portion inserted into an elongated device, in particular a medical device. Both signals interfere due to different optical paths and create an interference signal. From the interference signal, local strain data of the optical fiber can be derived, from which local curvature and/or torsion angle of the optical fiber can be obtained, enabling to reconstruct the shape of the fiber and consequently the shape of the device. In this way, the position and/or orientation of the medical device can be determined.

This requires, however, that the scattered device signal is in a polarization state non-orthogonal to the polarization state of the reference signal. Otherwise, no information can be retrieved since the interference signal is degraded due to polarization fading. Bending and torqueing of the medical device under test gives rise to birefringence, which changes this polarization state of the scattered or reflected device signal depending on the position of the reflection point within the medical device.

The birefringence is an effect related to changes in the refractive index, which cannot be decoupled from the change in mechanical length so that it influences the phase of the interference signal, leading to erroneous strain measurements. Moreover, due to the non-isotropic nature of birefringence, the interference signal depends on the exact polarization state of the input light signal and possibly also of the detector arrangement.

Figure 1:
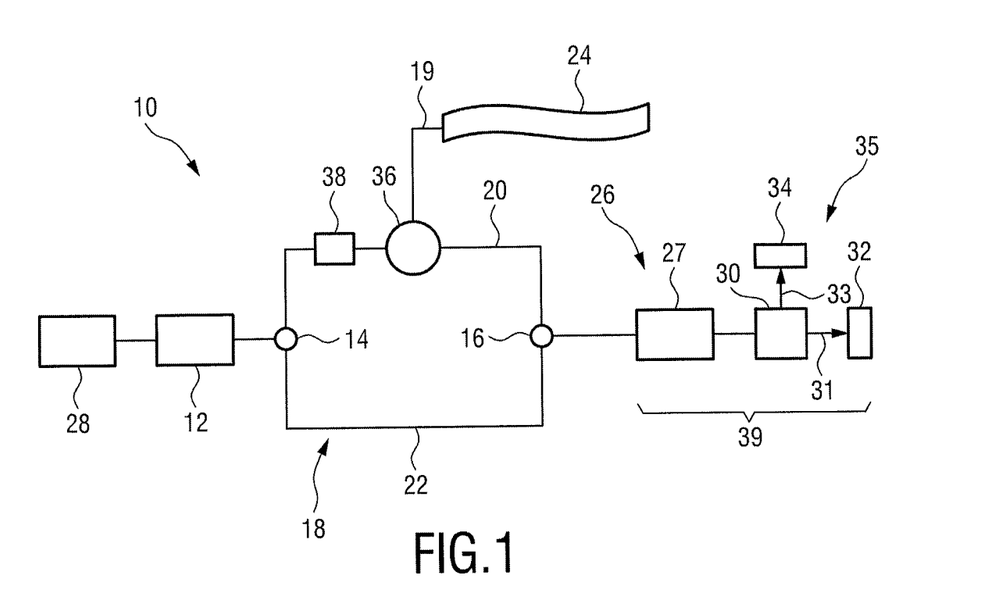
FIG. 1 shows a schematic block diagram of an optical shape sensing system in cooperation with a device.

In order to overcome the afore-mentioned problems, an optical shape sensing system 10 is proposed as shown in FIG. 1 comprising an input polarization controller 12, an interferometer unit 18 and a measurement branch 39. The input polarization controller 12 is configured to set an input polarization state for the input light signal using an input polarization setting.

The interferometer unit 18 comprises an optical coupler 14 for splitting the polarized input light signal into a device signal and a reference signal. The interferometer unit 18 further comprises a device branch 20 and a reference branch 22, the device branch 20 being connected to an optical fiber 19 which comprises a portion inserted into a device 24, in particular a medical device being an endoscope, a catheter or guidewires, The optical fiber 19 forms a part of the optical shape sensing system 10. The scattering or reflection may preferably be invoked by embedded periodical structures within the optical fiber 19, e.g. fiber Bragg gratings (FBG) or by non-periodic structures within the optical fiber 19 giving rise to random variations of the refractive index, e.g. Rayleigh scattering.

The interferometer unit 18 further comprises an optical coupler 16, wherein the reference branch 22 is configured to guide the reference signal directly to the optical coupler 16. The optical coupler 16 combines the reference signal and the device signal, which interfere with each other, leading to an output light signal being an interference signal.

The measurement branch 39 comprises an output polarization controller arrangement 26 comprising an output polarization controller 27 for setting an output polarization state of the output light signal using an output polarization setting. The measurement branch 39 further comprises a polarizing beam splitter 30 for splitting the polarized output light signal into two signal portions, each being in a corresponding signal portion polarization state. The measurement branch 39 further comprises a detector arrangement 35 comprising a first and second detector 32, 34, each for detecting a corresponding one of the two signal portions.

Preferably, the polarized output light signal is projected in two projection directions 31, 33 using the polarizing beam splitter 30, wherein each of the two detectors 32, 34 is configured to detect in a corresponding projection direction 31, 33. Further preferably, the two signal portion polarization states of the two signal portions are orthogonal to each other.

The optical fiber 19 inserted into the device 24 shown in FIG. 1 comprises a single core. Alternatively, the optical fiber 19 may comprise multiple cores, in particular at least four cores. In the case of multiple cores, each core is used for separately guiding a corresponding one of multiple device signal parts of the device signal. Preferably, the optical shape sensing system 10 comprises the same number of interferometer units 18 and/or measurement branches 39 as the number of cores of the optical fiber 19. Each core of the optical fiber 19 is configured to cooperate with a corresponding interferometer unit and measurement branch. This enables to distribute each reference signal in the multiple interferometers equally to the two detectors 32, 34 in each measurement branch 39.

Preferably, the optical shape sensing system 10 comprises a light source 28, in particular a tunable laser source (TLS) for generating the input light signal. The device branch 20 preferably comprises a circulator 36 to direct the device signal towards the device 24 and the scattered device signal further towards the optical coupler 16. Further preferably, the device branch 20 comprises a polarization controller 38 for polarizing the device signal before being guided to the device 24. The polarization controller 38 enables to account for the different birefringence properties of different interferometers in the case of multiple cores. For the single core case, in contrast, the input polarization controller 12 and the polarization controller 38 may be combined as one single optical device in order to achieve optimal birefringence correction. The optical connections between the various components of the optical shape sensing system 10 are realized preferably using optical fibers.

Figure 2:
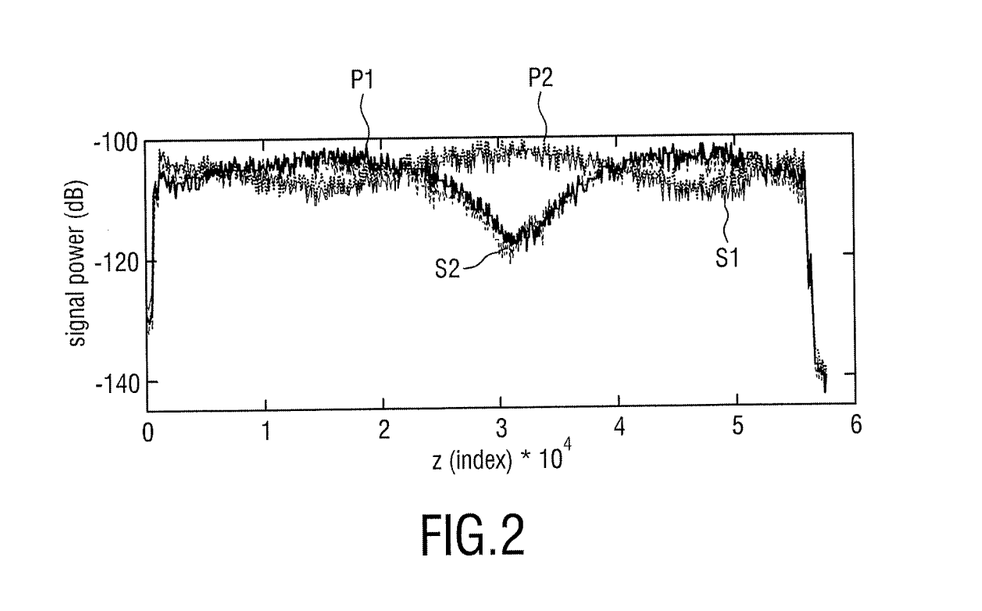
FIG. 2 shows schematically the result of a backscatter reflectometry measurement.

FIG. 2 shows schematically the result of a backscatter reflectometry measurement. A first input polarization setting is applied to the input polarization controller 12. Then, DC balancing is carried out for the output polarization controller 27 using only the reference signal. The DC balancing is utilized to determine an output polarization setting which enables a polarized reference signal projectable to the two detectors 32, 34 with equal signal amounts. After the DC balancing, both the device signal and the reference signal are used to perform the backscatter reflectometry measurement.

The wavelength of the input light signal is swept over a wavelength range, preferably from 1535 nm to 1555 nm. Two measurement signals are measured simultaneously by the first and second detector 32, 34, respectively. Both signals show an oscillation of the signal power, wherein the frequency of the oscillations depends on the sweeping rate of the wavelength on one hand, and on the length difference between the optical paths of the device signal and the reference signal on the other hand.

Since the optical path of the device signal depends on the scattering position within the fiber sensor portion of the optical fiber 19 inserted into the device 24, the oscillation frequency of the signals effectively depends on the position of the scattering position. By means of frequency analysis, in particular by applying a Fourier transformation, the reflectivity being the power of polarized output light signal detected by each detector 32, 34 is represented as a function of the scattering position along the fiber sensor portion of the optical fiber 19 within the device 24. The amplitude of the Fourier transformed signals P1 and S1 are depicted in FIG. 2.

Each wavelength sweep for obtaining both measurement traces S1, P1 is, without loss of generality, called a "measurement scan". After the first scan, a second scan is performed while a second input polarization setting is applied to the input polarization controller 12. The second input polarization setting is configured to enable a second input polarization state orthogonal to the first input polarization state of the first scan. The amplitudes of the measurement traces S2, P2 obtained in the second scan are also depicted in FIG. 2.

It can be seen therein that the measurement traces P1, S2 essentially overlap with each other. Further, the measurement traces P2, S1 overlap essentially with each other. In addition, the amplitudes of the traces S1, S2, P1, P2 are essentially the same at the beginning of each scan (z~0). The above results indicate that first, the two input polarization settings are properly chosen, and second, the DC balancing is properly performed.

It can be seen from FIG. 2 further that the maxima and minima of the measurement traces S1, P2 on one hand are located at different z-coordinates than the maxima minima of the traces S2, P1. This indicates imbalanced phases caused by birefringence, which needs to be corrected.

In the following, two methods will be discussed for signal analysis. The two methods are constructed in such a way that the result of the analysis is independent on the input polarization state of the polarized input light signal and the intermediate polarization state of the output light signal before being polarized by the output polarization controller 27. The analysis is performed in the time delay domain. The measured signals are originally a function of the optical frequency set in the light source 28. After a Fourier transformation, the measured signals are a function of delay time, i.e. the position along the elongated fiber portion within the device 24. In the following, the position along the elongated fiber portion is denoted as z-coordinate. In the time delay domain, the light scattered back after a scalar reflection remains fully polarized, albeit that during the traverse from the light source 28 to the detectors 32, 34 the orientation and the ellipticity of the polarization will change. The result of the polarization is dependent on the z-coordinate of the scattering position within the device 24.

The polarization state of the light signal at a position immediately after the optical coupler 16 and in the front of the output polarization controller 27 can be described by the following two Jones vectors:

$$y_1 = \begin{pmatrix} 1 \\ 0 \end{pmatrix}, y_2 = \begin{pmatrix} 0 \\ 1 \end{pmatrix} \quad (1)$$

With a unit to coordinate transformation, it can be ensured that the polarization state of the light signals before being polarized by the output polarization controller 27 is characterized by a polarization direction lying on the principle axis. The two input polarization states are also orthonormal and can generally be expressed as follows:

$$x_1 = \frac{1}{\sqrt{1+\chi\cdot\chi^*}}\begin{pmatrix} 1 \\ \chi \end{pmatrix}, x_2 = \frac{1}{\sqrt{1+\chi\cdot\chi^*}}\begin{pmatrix} \chi^* \\ -1 \end{pmatrix} \quad (2)$$

The quantity $\chi$ is complex and is a function of the ellipse axis angle $\theta$ and the ellipticity angle $\varepsilon$ as given by:

$$\chi = \frac{\tan\theta + i\tan\varepsilon}{1 - i\tan\theta\tan\varepsilon} \quad (3)$$

Figure 3:
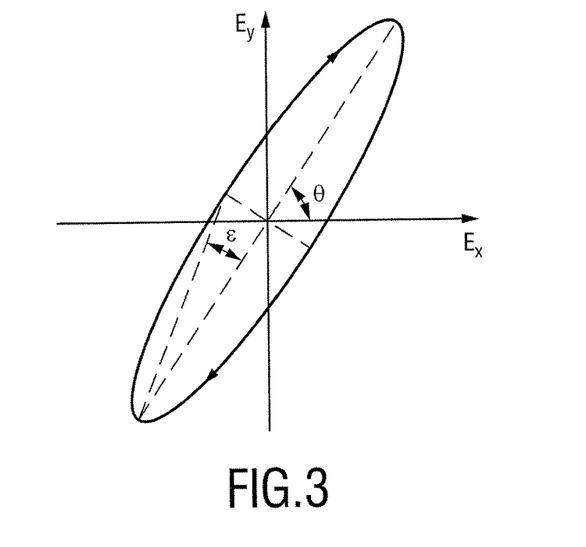
FIG. 3 shows an illustrative visualization of electric field vectors of elliptically polarized light.

The physical meaning of the angles $\theta$ and $\varepsilon$ is illustratively shown in FIG. 3, which shows electric field vectors $E_x$ and $E_y$ of elliptically polarized light propagating in the z-direction.

The input polarization states $x_1$ and $x_2$ are chosen that the reference signal is measured by the two detectors 32, 34 with equal signal strengths. This condition is fulfilled, when $|E_x|^2=|E_y|^2=0.5$. The afore-mentioned condition corresponds to:

$$\chi\cdot\chi^*=1 \quad (4)$$

Figure 4:
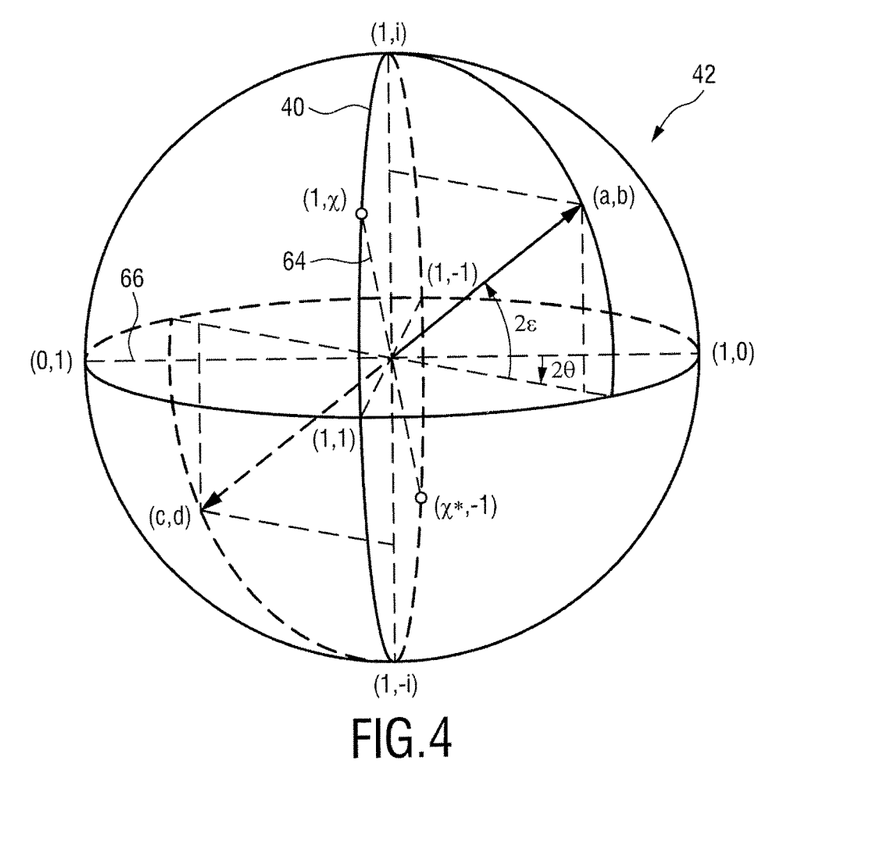
FIG. 4 shows an illustrative visualization of a Poincaré sphere.

Equation (4) means that the vectors representing the input polarization states lie on a circle 40 on a Poincaré sphere 42 shown in FIG. 4, wherein the circle 40 goes through the points with the coordinates (1, 1) and (1, −1) on the equator representing lineally polarized light at ±45°, and the points with the coordinates (1, i) and (1, −i) at the north- and south pole representing circularly polarized light.

The above analysis assumes that the light traversing through the reference branch 22 of the interferometer unit 18 will not alter its polarization state, which means that the reference branch 22 does not contain any parts that exhibit birefringence. This, however, is not given in general. One can, however, also regard equations (2-4) as if they were describing input polarization states not at the position immediately before the optical splitter 14, but at a position immediately after the optical coupler 16 and/or immediately before the output polarization controller 27. The effective birefringence of the device branch 20 is then the actual birefringence of the device branch 20 "compensated" by the birefringence of the reference branch and corresponds to the case as if the reference signal would be guided backwards through the reference branch 22, reflect from the input polarization controller 12 and propagate to the measurement branch consisting of the optical elements downstream of the optical coupler 16.

Consequently, neglecting the birefringence of the reference branch 22 is effectively the same as adding the birefringence of the reference branch 22 while assuming an opposite direction relative to the birefringence of the device branch 20. The effective birefringence of the device branch 20 and compensating reference branch 22 can be described by a Jones matrix:

$$\overline{\overline{T}}(z) = \begin{pmatrix} T_{11}(z) & T_{12}(z) \\ T_{21}(z) & T_{22}(z) \end{pmatrix} = \begin{pmatrix} T_{11}(z) & T_{12}(z) \\ -T_{12}^*(z) & T_{11}^*(z) \end{pmatrix} \quad (5)$$

The most right hand side of equation (5) expresses two of the general symmetry relations of a Jones matrix for an elliptic retarder: $T_{22}^*=T_{11}$ and $T_{21}^*=-T_{12}$. The third symmetry relation expresses the fact that an elliptic retarder performs a unitary transformation without loss of light:

$$\det(T(z))=T_{11}(z)T_{22}(z)-T_{12}(z)T_{21}(z)=|T_{11}(z)|^2+|T_{12}(z)|^2=1 \quad (6)$$

The Jones matrix T contains only 2 independent complex coefficients with an additional constraint that the determinant is unity. Therefore, there are in practice only three independent quantities. These quantities are the two angles of orientation of the principle axis of the birefringence and the amount of rotation around this axis, i.e. magnitude of the birefringence. Each matrix element $T_{xx}$ can be expressed as a function of these three quantities. It is assumed that the birefringence is sufficiently small meaning that the total effective birefringence is only a slowly varying function of position within the elongated fiber portion. This corresponds to slowly varying the birefringence as a function of wavelength, i.e. the interferometer is an effective elliptic retardation plate of single wavelength value. The Jones matrix T transforms the input polarization states $x_1$ and $x_2$ in two intermediate polarization states of the output light signal being an interference signal from the device and reference branches 20, 22 $(a(z),b(z))^T$ and $(c(z),d(z))^T$, in which the Fresnel reflection coefficient $A(z)$ and the phase retardation of the reflection point $\tau(z)$ will be incorporated.

$$\begin{pmatrix} a(z) \\ b(z) \end{pmatrix} = x_1^{*T}\cdot\overline{\overline{T(z)}}\cdot x_1 A(z)e^{i\tau(z)} = \begin{pmatrix} T_{11}(z) + \chi T_{12}(z) \\ -\chi^* T_{12}^*(z) + T_{11}^*(z) \end{pmatrix}\frac{A(z)}{2}e^{i\tau(z)} \quad (7)$$

$$\begin{pmatrix} c(z) \\ d(z) \end{pmatrix} = x_2^{*T}\cdot\overline{\overline{T(z)}}\cdot x_2 A(z)e^{i\tau(z)} = \begin{pmatrix} T_{11}(z) - \chi\cdot T_{12}(z) \\ \chi^* T_{12}^*(z) + T_{11}^*(z) \end{pmatrix}\frac{A(z)}{2}e^{i\tau(z)}$$

From equations (7) one immediately recognizes two relations between the four measured signals:

$$d(z)^* = a(z) \rightarrow |a(z)| = |d(z)|$$

$$c(z)^* = b(z) \rightarrow |b(z)| = |c(z)| \quad (8)$$

The relations set out in equations (8) are a consequence of the orthogonality of the input polarization states $x_1$ and $x_2$. After the initial choice of input polarization state $x_1$ having the constraint that the reference signal is detectable by the detectors 32, 34 with equal signal amounts, one has to determine the orthogonal input polarization state $x_2$. This is accomplished by plotting the absolute value of the four signals while the device under test exhibits birefringence and adjusting the input polarization controller 12 for the state $x_2$ until the relations set out in equations (8) are fulfilled.

The object of the signal analysis is to retrieve the position dependent Fresnel coefficient $A(z)$ and the phase factor $\exp(i\tau(z))$ from the four signals $a(z)$, $b(z)$, $c(z)$ and $d(z)$ irrespective of the input polarization quantity $\chi$ or the amount and orientation of the effective birefringence as expressed by the Jones matrix T. There are various methods to perform this task, from which two are described as follows:

Method I:

Two complex quantities can be defined as:

$$r_1(z)e^{j\phi_1(z)} = (T_{11}(z) + \chi T_{12}(z))/\sqrt{2}$$

$$r_2(z)e^{j\phi_2(z)} = (-\chi^* T_{12}^*(z) + T_{11}^*(z))/\sqrt{2} \quad (9)$$

Since an elliptic retarder does not change the total amount of light ($\det(T) = 1$) and the input polarization contributes equally to the signals detected by both detectors ($\chi\chi^* = 1$), the Jones vector of equation (9) is normalized, i.e. $|r_1(z)|^2 + |r_2(z)|^2 = 1$. The birefringence phase factors $\phi_1(z)$ and $\phi_2(z)$ can be determined using:

$$\phi_{ad} \stackrel{def}{=} \text{angle}(a(z) \cdot d(z)^*) = 2\phi_1(z)$$

$$\phi_{bc} \stackrel{def}{=} \text{angle}(b(z) \cdot c(z)^*) = 2\phi_2(z) \quad (10)$$

A new vector can be defined as:

$$\begin{pmatrix} p(z) \\ q(z) \end{pmatrix} \stackrel{def}{=} \begin{pmatrix} ae^{-i\phi_{ad}/2} + de^{+i\phi_{ad}/2} \\ be^{-i\phi_{bc}/2} + ce^{+i\phi_{bc}/2} \end{pmatrix} = \begin{pmatrix} r_1(z) \\ r_2(z) \end{pmatrix} A(z) e^{i\tau(z)} \quad (11)$$

The amplitude of the Fresnel coefficient describing the scalar scattering and the phase delay associated with this scattering process containing the strain information can be recovered from equation (11):

$$A(z) = \sqrt{p(z) \cdot p(z)^* + q(z) \cdot q(z)^*}$$

$$\tau(z) = \text{angle}(p(z)) = \text{angle}(q(z)) \quad (12)$$

Method II:

With a unitary transformation a Jones vector can be rotated in such a way that it is parallel to one of the basis vectors of the polarization coordinate system:

$$\begin{pmatrix} S_1(z) \\ 0 \end{pmatrix} = \begin{pmatrix} e^{i\phi(z)}\cos\theta(z) & e^{i\gamma(z)}\sin\theta(z) \\ -e^{-i\gamma(z)}\sin\theta(z) & e^{-i\phi(z)}\cos\theta(z) \end{pmatrix} \begin{pmatrix} a(z) \\ b(z) \end{pmatrix} \quad (13)$$

The matrix of equation (13) fulfils all symmetry requirements of a Jones matrix describing an elliptic retarder: the determinant equals unity, the diagonal matrix elements are complex conjugate of each other and one off-diagonal element is the negative complex conjugate of the other. The quantities $\theta(z)$, $\phi(z)$ and $\gamma(z)$ have a non-trivial relation to the angles associated with a rotation in the Poincaré sphere. The values for the angles $\theta(z)$, $\phi(z)$ and $\gamma(z)$ are inferred from:

$$e^{i(\phi(z)-\gamma(z))} \tan\theta(z) = \frac{b(z)}{a(z)} \quad (14)$$

$$\tan\theta(z) = \left|\frac{b(z)}{a(z)}\right|$$

$$\phi(z) - \gamma(z) = \text{angle}\left(\frac{b(z)}{a(z)}\right)$$

The second wavelength sweep is performed with an input polarization state orthogonal to that of the first wavelength sweep. Consequently, the Jones vector measured for the second scan is perpendicular to that for the first scan. The polarization of the reference branch 22 is also rotated. This means that the points (a,b) and (c,d) on the surface of the Poincaré sphere 42 in FIG. 4 representing the signal portion polarization states correspond to four different measured light intensities and not the electric field components of two Jones vectors. On the other hand, it is known that $a = d^*$ and $b = c^*$, so that the state represented by (a,b) is orthogonal to that represented by (c,−d). Rotation of the latter vector with the same unitary matrix as in equation (13) results in a vector parallel to the second basis vector:

$$\begin{pmatrix} 0 \\ S_2(z) \end{pmatrix} = \begin{pmatrix} e^{i\phi(z)}\cos\theta(z) & e^{i\gamma(z)}\sin\theta(z) \\ -e^{-i\gamma(z)}\sin\theta(z) & e^{-i\phi(z)}\cos\theta(z) \end{pmatrix} \begin{pmatrix} c(z) \\ -d(z) \end{pmatrix} \quad (15)$$

In analogy to equation (14) one obtains from equation (15):

$$e^{i(\gamma(z)-\phi(z))} \tan\theta(z) = \frac{c(z)}{d(z)} \quad (16)$$

$$\tan\theta(z) = \left|\frac{c(z)}{d(z)}\right|$$

$$\gamma(z) - \phi(z) = \text{angle}\left(\frac{c(z)}{d(z)}\right)$$

Combining Equations (14-16) yields:

$$S_1(z) = (e^{i(\phi(z)-\gamma(z))} \cos\theta(z) a(z) + \sin\theta(z) b(z)) e^{i\gamma(z)} = \frac{b(z)}{\sin\theta(z)} e^{i\gamma(z)} \quad (17)$$

$$S_2(z) = (-\sin\theta(z) c(z) - e^{i(\gamma(z)-\phi(z))} \cos\theta(z) d(z)) e^{-i\gamma(z)} = -\frac{c(z)}{\sin\theta(z)} e^{-i\gamma(z)}$$

The quantities $S_1(z)$ and $S_2(z)$ represent the scattering reflection coefficient multiplied with the delay phase factor, and should be independent of the birefringence. Consequently, they should be identical, so that the angle $\gamma(z)$ can be retrieved from:

$$2\gamma(z) = \text{angle}(-c(z) \cdot b(z)^*)$$

$$2\phi(z) = \text{angle}(-d(z) \cdot a(z)^*) \quad (18)$$

Inserting the value for γ(z) from Equation (18) in either of the equations (17) yields the scalar Fresnel scattering coefficient. Similarly to Method I the delay phase of the scalar Fresnel scattering coefficient is determined to within a constant phase value $\phi_0$ independently of position.

Equation (18) has great similarity to equation (10) of Method I, whereas the cos(θ(z)) and sin(θ(z)) of Method II play the same role as the $r_1(z)$ and $r_2(z)$ terms of equation (9) from Method I.

The optical shape sensing systems known in the prior art have the following drawbacks. First, the two orthogonal input polarization states cannot be properly applied. In particular, the difference of amplitudes of the light signal detected by one detector in one scan differs from that of the light signal detected by the other detector in the other scan. Such differences are merit functions that need to be nulled. The nulling achieved by the known systems is, however, by trial and error.

Second, the known systems do not make use of a polarization controller 27 but achieve a DC balancing by rotation of polarizing beam splitter 30. Consequently only one out of an infinite amount of possible DC balancing points can be obtained.

Third, even when the orthogonal input polarization states could be properly set and the DC balancing properly performed, it is not guaranteed that the device signal is projectable to the two detectors with equal signal amounts. A finite amount of birefringence in the lead wires towards and from the circulator 36 may cause an unequal distribution and thus an unequal amount of interference signals, leading to insufficient or erroneous AC balancing.

Fourth, in the presence of birefringence in the device 24, the output polarization state of the light signal depends on the position of the reflection point within the fiber portion within the device 24. Consequently, the amplitudes of signal portions detected by the two detectors 32, 34 vary as a function of a position coordinate. Even when polarization fading due to birefringence is avoided, which means that the total amount of measured signal on both detectors stays constant irrespective of birefringence and the input polarization state, the signal portion detected by one of the detectors may be much smaller than that of the other detector for a particular reflection point within the device 24. This leads to a strongly reduced signal-to-noise (SNR) ratio for two out of the four signals obtained in two measurement scans. Consequently, the accuracy of the birefringence correction is significantly reduced.

Moreover, the phase error which needs to be corrected is maximal at the afore-mentioned particular reflection point at which the signal portion detected by one of the two detectors becomes much smaller. This can be seen from the schematic graphs shown in FIG. 5, which shows a simulation of polarization fading.

In FIG. 5A-1, three phase signal traces 44, 46, 48 are shown as a function of the ellipse axis angle θ (FIG. 3). The first and second phase signal traces 44, 46 are obtained each from one of both detectors, wherein the third phase signal trace 48 is the difference between the first and the second phase signal traces 44, 46. In FIG. 5A-2, two amplitude traces 50, 52 are shown as a function of the ellipse axis angle θ. The first amplitude trace 50 is obtained from the detector from which the first phase signal trace 44 is obtained. The second amplitude trace 52 is obtained from the detector from which the second phase signal trace 46 is obtained.

In FIG. 5B-1, three phase signal traces 54, 56, 58 analogous to the traces in FIG. 5A-1 are depicted as a function of the ellipticity angle ε (FIG. 3). FIG. 5B-2 shows two amplitude traces 60, 62 analogous to the traces in FIG. 5A-2 depicted as a function of the ellipticity angle ε. FIGS. 5A-1, A-2 shows therefore that birefringence causes a change in the ellipse axis angle θ, wherein FIGS. 5B-1, B-2 shows that birefringence causes a change in the ellipticity angle ε. The influence of such a change on the phase and amplitude signal is similar for both the ellipse's angle θ and the ellipticity angle ε.

Figure 5:
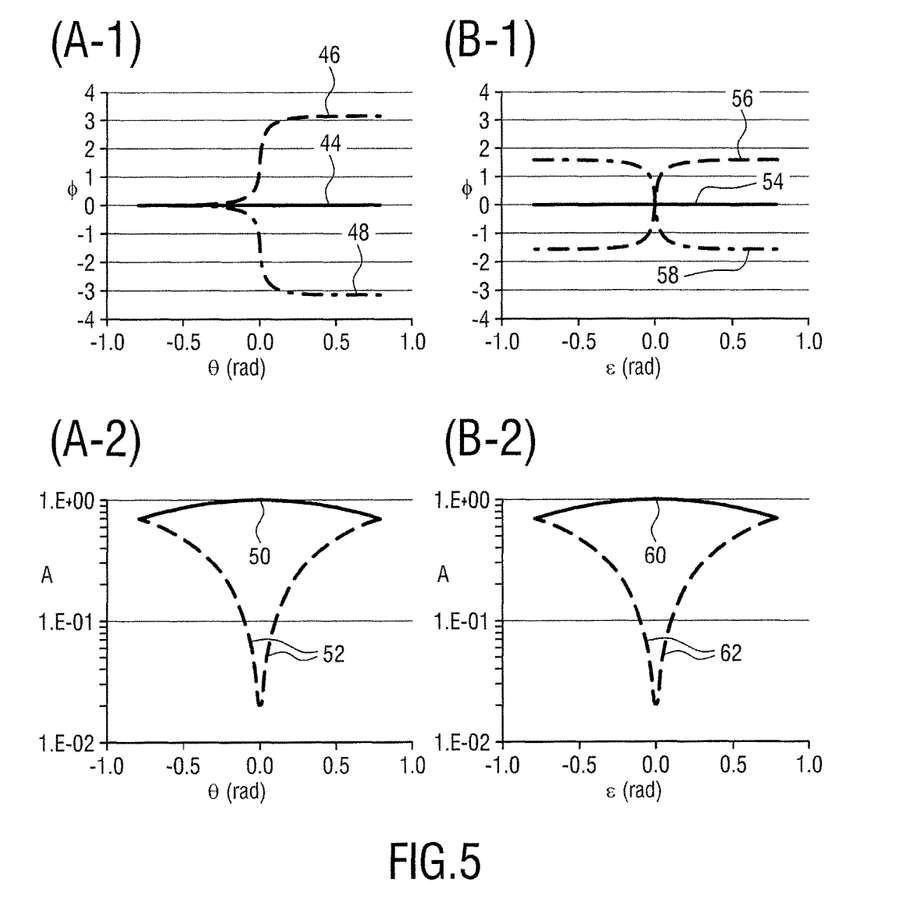
FIG. 5 shows schematically the result of a simulation of polarization fading.

As can be seen in FIGS. 5B-1, B-2, the smaller the ellipticity angle ε gets, the sharper a transition of the third phase signal trace 58 becomes and the smaller the amplitude of the second amplitude trace 62 in FIG. 5B-2 becomes. Consequently, a large gradient in the phase difference between the two measured signals is present when the amplitude of one of them is strongly reduced. When one of the detectors detect a signal with small amplitude it means that the principle axis of the polarization state of the detected signal portion nearly coincides with one of the axes of the polarizing beam splitter 30, meaning that the angle θ is small and that the ellipticity ε (FIG. 3) is small. When performing two measurement scans with two orthogonal input polarization states, a small change in θ around 0 will have the effect that the phase of one of both detected signal portions has an opposite sign compared to the phase of the other detected signal portion, giving rise to a phase shift of π between the two signal portions. This effect can be seen in the two left graphs (A-1, A-2) of FIG. 5. Similarly, a small change in ε around 0 will give rise to a phase shift of π between the two signal portions, as can be inferred from the two right graphs (B-1, B-2) of FIG. 5.

In order to overcome the afore-mentioned disadvantages, the input polarization controller 12 is configured to set two pairs of input polarization states, or the output polarization controller 27 is configured to set two output polarization states each for enabling a corresponding one of two pairs of signal portion polarization states, wherein each pair of input or signal portion polarization states are representable by a corresponding one of two axes in a Poincaré sphere perpendicular to each other.

Four settings are applied to the input polarization controller 12 to set the two pairs of input polarization states, wherein preferably the same setting is applied to the output polarization controller 27, resulting in four measurement scans. Each input polarization state is represented by a vector or a point of the Poincaré sphere, wherein the vectors or points representing each pair of input polarization states define an axis. The two polarizations of one pair of input states have orthogonal polarizations and consequently are positioned on opposite sides of the Poincaré sphere, so they form an axis. The second pair of input states form a second axis which is preferably orthogonal to the first axis. The output states measured by the two detectors and determined by the polarization controller 27 and beams splitter 30 are also represented by two points on opposite sides of the Poincaré sphere forming a third axis. Preferably, this third axis is orthogonal to the previous two in order to achieve DC balancing for all the 4 scans. The three said axis form an orthogonal basis so that the full Poincaré sphere is addressed for optical shape sensing.

Alternatively, two settings are applied to the output polarization controller 27 to set the two output polarization states, each for two settings applied to the input polarization controller 12, resulting in four measurement scans. Each signal portion polarization state is represented by a vector or a point of the Poincaré sphere, wherein the vectors or points representing each pair of signal portion polarization states enabled by the corresponding output polarization state define an axis. In this way, at least two axes in a Poincaré sphere perpendicular to each other are addressed by the measurement branch. The two input polarizations define a third axis on the Poincaré sphere. Preferably, these three axes on the Poincaré sphere define an orthogonal basis, so that the full Poincaré sphere is addressed for optical shape sensing.

Figure 6:
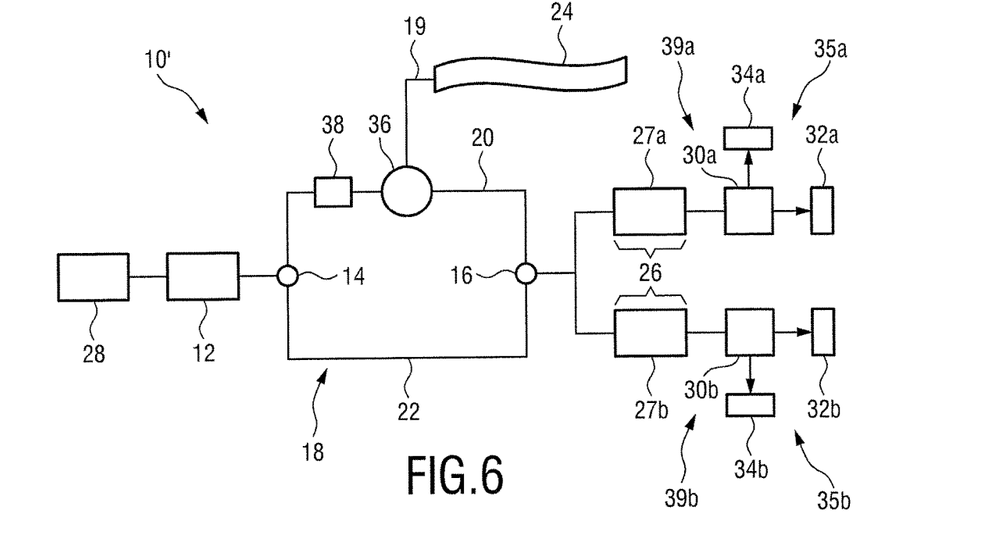
FIG. 6 shows a schematic block diagram of an optical shape sensing system comprising two measurement branches in cooperation with a device.

In a preferable embodiment shown in FIG. 6, the optical shape sensing system 10' is configured similarly to the optical shape sensing system 10 shown in FIG. 1, except that the system shown in FIG. 6 comprises two separate measurement branches 39a, b. The optical shape sensing system 10' is configured such that the output light signal comprises two separate signal parts, wherein each output signal part is guided to a corresponding measurement branch 39a, b. The two polarization controllers 27a, b apply to both signal parts each a different output polarization setting in order to achieve two output polarization states. The polarizing beam splitters 30a, b then split each polarized signal part into two signal portions detected by a corresponding detection arrangement 35a, b, resulting in two pairs of signal portion polarization states. In this way, at least two axes in a Poincaré sphere perpendicular to each other are addressed by the two measurement branches, wherein each axis represents a pair of signal portion polarization states. Advantageously, the two measurement branches may be operated simultaneously, so that only two measurement scans need to be performed for acquiring the same amount of results as in the previous two embodiments requiring four measurement scans.

As shown in FIG. 4, two input polarization states are represented by the points $(1, \chi), (\chi^*, -1)$ defining an axis 64 in the Poincaré sphere 42. The two detectors 32a, 34a of the first measurement branch 39a detect each a signal portion polarization state represented by the points (0, 1) and (1, 0), respectively, defining an axis 66 perpendicular to the axis 64. Once the two orthogonal axes 64, 66 are chosen, a third axis which corresponds to the signal portion polarization states detected by the second measurement branch 39b can be determined to be perpendicular to both axes 64, 66. This representation based on Poincaré sphere is analogously applicable to the optical shape sensing system 10 shown in FIG. 1. In the following, reference will be made to the system of FIG. 1.

Preferably, the output polarization controller arrangement 27 is configured to apply three different output polarization settings. Two output polarization settings are applied so that the polarized reference signal is projectable to the two detectors 32, 34 with equal signal amounts. The remaining third output polarization setting is applied so that the polarized reference signal is projectable to only one of both detectors 32, 34 and is used to calibrate the input polarization controller 12.

Without loss of generality, the afore-mentioned third output polarization setting is called "100-0 split" setting, wherein the two other output polarization settings are called the first and the second "50-50 split" setting. The "100-0 split" setting can be obtained in the following way: After calibration the polarization controller 27 can be adjusted to address sufficiently different polarizations probing half of the Poincaré sphere. About 30 settings will suffice from which a further optimization can be obtained by e.g. a steepest descent method. The determination of the first 50-50 split setting is based on that every output polarization state that is projectable to both detectors with equal signal amounts is represented by a vector orthogonal to another vector representing an output polarization state fully projectable to only one detector. Preferably, the first 50-50 split setting is chosen to set an output polarization state orthogonal to the output polarization state enabled by the 100-0 split setting, which is straightforward after calibration of the polarization controller 27.

Figure 7:
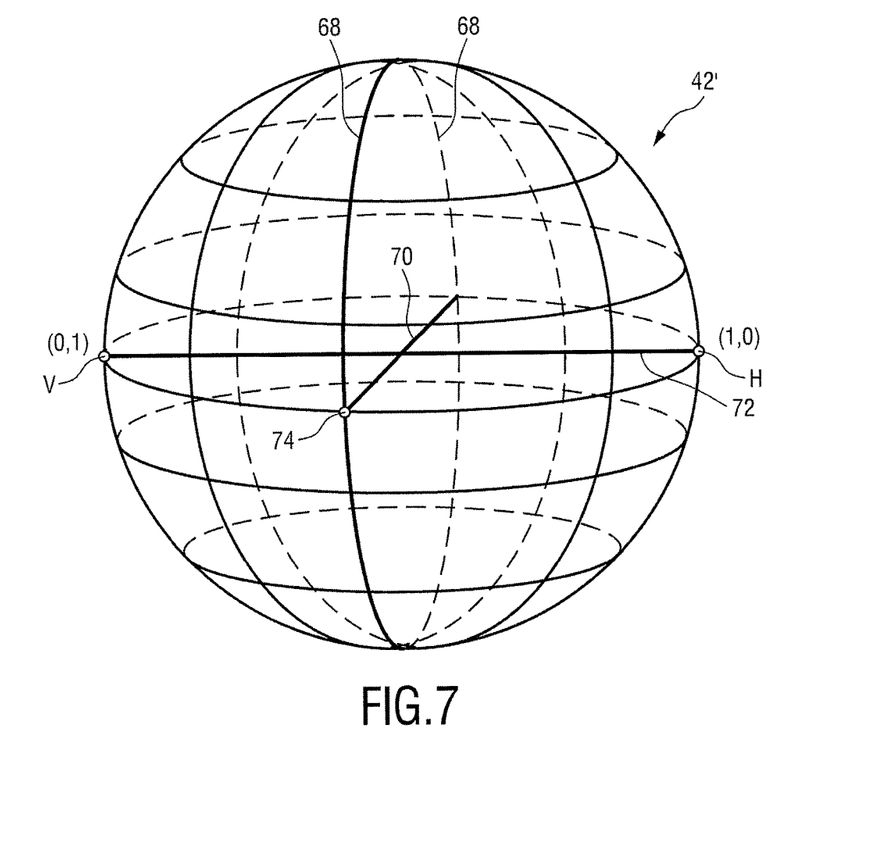
FIG. 7 shows an illustrative visualization of polarization settings.

The second 50-50 split setting can be determined as follows: without loss of generality, it can be assumed that the two detectors 32, 34 detect two signal portion polarization states represented by the points H (0, 1) and V (1, 0) in the Poincaré sphere 42', respectively, as shown in FIG. 7. The two points H, V define an axis 72. The output polarization states that are projectable to both detectors with equal signal amounts are then indicated by the circle 68 perpendicular to the axis 72. The output polarization state set by the first 50-50 split setting is represented by a point 74 on an axis 70.

The output polarization state set by the second 50-50 split setting may be achieved by rotating the state represented by the point 74 around one of the two axes 70, 72. Preferably, the second 50-50 split setting is chosen to set an output polarization state represented by a vector which is the same vector as the one representing the output polarization state set by the first 50-50 split setting, followed by a rotation of 90° around the axis 70 traversing the point representing the output polarization state set by the first 50-50 split setting. In this way, the second 50-50 split setting enables to project the reference signal to both detectors with equal signal amounts, wherein the ratio of the device signal amounts detected by both detectors is changed compared to the first 50-50 split setting. When rotating over 90 degrees around axis 70 the signal from the reference is not altered. However, non-aligned polarizations from the device branch causing fading on one of the detectors will be rotated.

Preferably, two methods can be applied to maximize the SNR in the optical shape sensing. The first method includes using two output polarization settings for the output polarization controller 27, such as the two 50-50 split settings described above, combined with one of two different input polarization settings for each of two scans. This method corresponds to rotating the output polarization state. The second method includes using one output polarization setting for the output polarization controller 27 combined with two different pairs of input polarization settings for the input polarization controller 12. The second method corresponds to rotating the input polarization state. In the following, the first method will be explained.

It is known that the amount of birefringence in the optical shape sensing system 10 and/or the device 24 depends on the wavelength of the input light signal. Over a certain wavelength span, the difference in the amount of birefringence of a fiber is, among others, dependent on the length of the fiber. The amount of the fiber between the light source 28 and the input polarization controller 12 as well as between the output polarization controller 27 and the polarizing beam splitter 30 can be negligibly short. Preferably, the amount of fiber in the reference branch 22 and in the device branch 20 has essentially the same length. This has the advantage that the signal component resulting from the device branch 20 detected by the detectors 32, 34 has a frequency that is sufficiently low so that the requirements regarding the signal processing speed and the sharpness of the band pass filter is reduced. This reduces complexity and cost of the optical shape sensing system 10.

It is preferable to either avoid or compensate the wavelength dependency of the birefringence, so that the reference signal can be projected to both detectors 32, 34 with equal signal amounts for the entire wavelength scan, in which the light source 28 is swept. This can be achieved by optimizing the output polarization settings of the output polarization controller arrangement 26 during a wavelength sweep.

Alternatively, this can also be achieved based on the nature of birefringence in the reference branch 22. For a relatively small wavelengths span, the axis of the birefringence in the reference branch 22 remains approximately constant, while the amount of birefringence is wavelength-dependent. If the input polarization state has a polarization direction that is aligned to the axis of the birefringence, the input polarization state will approximately not rotate during the wavelength sweep. Depending on the input polarization state, the angle between the output polarization state corresponding to a wavelength of 1535 nm and the output polarization state using a wavelength of 1555 nm can vary from less than 1° to 15° over the Poincaré sphere.

To obtain the input polarization setting of the input polarization controller 12 such that the reference signal is in an eigen polarization mode, up to $15^3$ of different input polarization settings can be set by the input polarization controller 12. For every input polarization setting, at least three equidistant wavelengths can be applied with the light source 28, so that various ratios between the signal amounts detected by both detectors 32, 34 is achieved. The difference between the lowest and the highest ratio can be obtained for each input polarization setting, and compared between different input polarization settings. The input polarization setting that achieves the smallest difference between the afore-mentioned lowest and highest ratio can be chosen as an optimum input polarization setting. A polarimeter can be connected, preferably in place of the detector 32, 34, to measure the output polarization state at various wavelengths.

Another preferable procedure of obtaining an optimal input polarization setting of the input polarization controller 12 makes use of the fact that the differences between the afore-mentioned lowest and highest ratio, the ratio being between the signal amounts detected by both detectors 32, 34, is reduced when the polarized input light signal is in a polarization state close to the eigen polarization state of the optical fiber in the reference branch 22.

Only when using two orthogonal input polarization states can both input polarization states define an axis in the Poincaré sphere aligned with the axis of birefringence. When using two pairs of orthogonal input polarization states, only one orthogonal pair can be aligned to the axis of birefringence. Further, using only one pair of orthogonal input polarization states enables to completely avoid birefringence in the reference branch 22.

Preferably, the polarization controller 38 is configured to achieve a scattered or reflected device signal that is projectable to both detectors 32, 34 with equal signal amounts. This means that the reflected device signal is in a polarization state that is representable by a point lying on the circle 68 in FIG. 7, which is arranged in the middle between the points H, V, which represent two polarization states projectable fully to either of both detectors 32, 34. In the implementation which uses only one pair of orthogonal input polarization states, the polarization controller 38 is set in such a way that the output polarization state of the device signal corresponds to that of the reference signal rotated around an axis coinciding the vector that represents the output polarization state of the reference signal.

The output polarization state of the device signal set in this way is represented by a point lying on the circle 68 in FIG. 7. This means that using the second 50-50 split setting of the output polarization controller 27, the polarized device signal is projectable to both detectors 32, 34 with equal signal amounts only when its polarization state is the same as that of the reference signal or orthogonal to the latter state.

The following procedure is proposed for AC balancing, i.e. determining an output polarization setting for the output polarization controller 27 to enable the polarized device and/or output signal is projectable to both detectors 32, 34 with equal signal amounts. First, apply a first input polarization setting to the input polarization controller 12 combined with a first output polarization setting to the output polarization controller 27, so that the polarized reference signal is projectable to one detector, for instance the second detectors 34. The polarization state of the reference signal is thus aligned to that detected by the second detector 34. Second, a measurement scan involving both the device and reference signals is repeatedly performed by sweeping the wavelength of the light source 28, wherein the device signal is extracted from the output signal while varying the setting of the polarization controller 38. The situation, in which the polarization state of the device signal is orthogonal to that of the reference signal is achieved when the amplitude of the extracted device signal at the beginning of the elongated fiber portion, in particular a fiber Bragg grating (FBG), is close to zero. Third, the setting for the output polarization controller 27 is determined for DC balancing. By the end of the third step, AC balancing is achieved for all four measurement scans.

Figure 8:
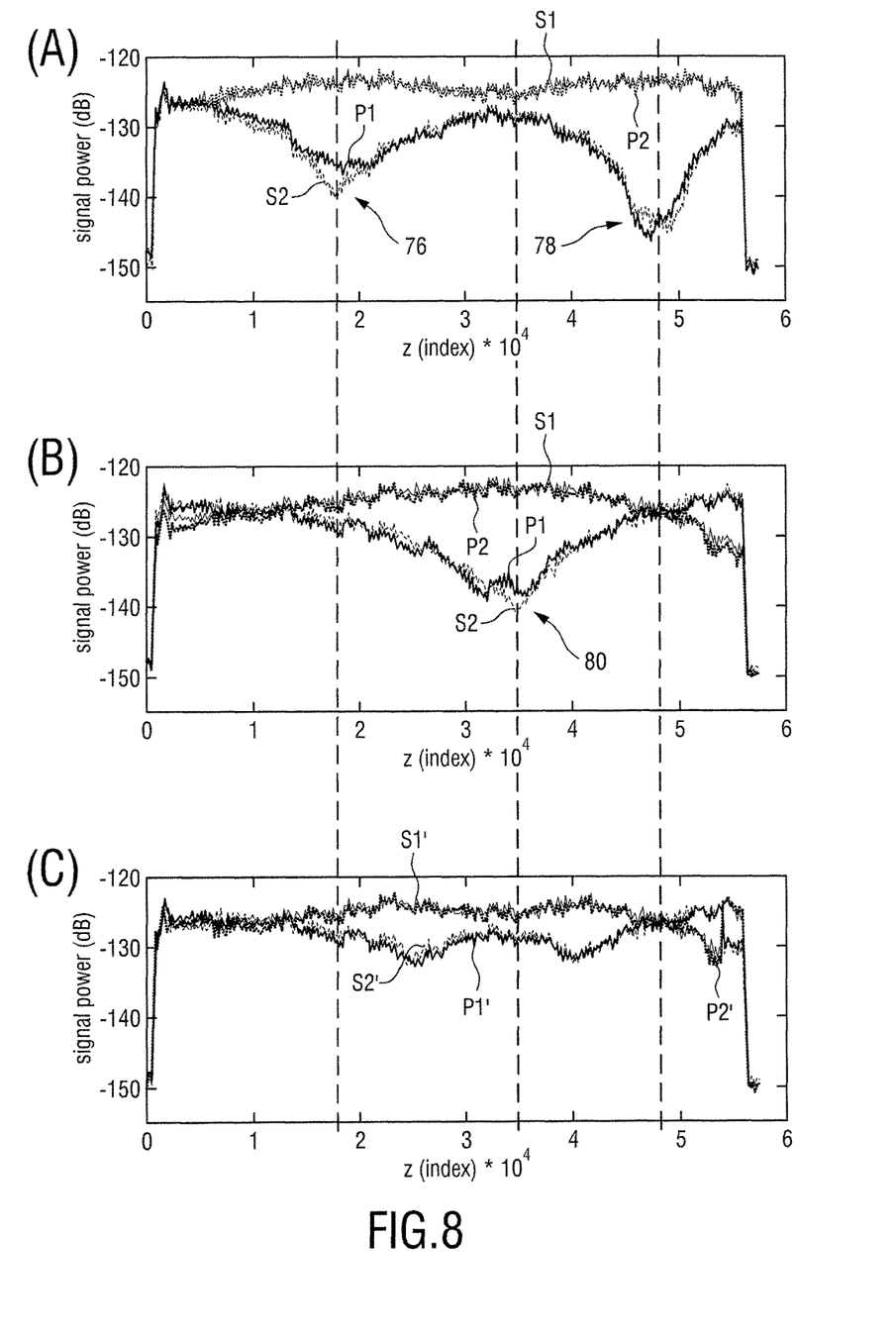
FIG. 8 shows schematically the result of another backscatter reflectometry measurement.

FIG. 8 shows the result of another backscatter reflectometry measurement. FIGS. 8A, B shows four measurement traces S1, P1, S2, P2 obtained analogously to the measurement traces shown in FIG. 2. Before obtaining the measurement traces, the optical shape sensing system 10 is calibrated so that the polarized output light signal can be projected to the two detectors 32, 34 with equal signal amounts. This calibration is performed at a constant wavelength of 1545 nm. Then, the wavelength of the input light signal is swept from 1535 nm to 1555 nm. The backscatter reflectometry measurement can be performed using one or more cores of an optical fiber, wherein the measurement traces of a central core of the multi-core optical fiber are shown in FIG. 8.

The measurement traces S1, P1 shown in FIG. 8A are obtained in a first measurement scan using a first input polarization setting of the input polarization controller 12 combined with a first output polarization setting of the output polarization controller 27. The measurement traces S2, P2 of FIG. 8A are obtained in a second measurement scan using a second input polarization state of the input polarization controller 12 combined with the first output polarization setting of the output polarization controller 27. The two input polarization settings are used to set two input polarization states orthogonal to each other. A DC balancing is performed for the reference signal under the first input polarization setting in order to determine the first output polarization setting.

The measurement traces shown in FIG. 8B are obtained using the same input polarization settings for the input polarization controller 12, each combined with a second output polarization setting for the output polarization controller 27 determined analogously to the first output polarization setting.

The first and the second output polarization settings are used to set two output polarization states each giving rise to two signal portion polarization states represented by an axis on the Poincaré sphere, wherein the two axes are perpendicular to each other. Each of the measurement traces shown in FIGS. 8A, B is obtained by further applying a Fourier transformation.

It can be seen in FIG. 8A that the measurement traces S1, P2 essentially overlap with each other, wherein the measurement traces P1, S2 overlap essentially with each other. It can also be seen that the four traces S1, P1, S2, P2 have essentially the same amplitude at the beginning of each measurement scan. Similar observations can also be made in FIG. 8B. This indicates that both output polarization settings of the output polarization controller 27 have been properly chosen so that the polarized signal portions are detected by both detectors 32, 34 with essentially equal signal amounts. Further, this also indicates that the first and the second input polarization settings of the input polarization controller 12 are properly chosen so that the corresponding input polarization states are orthogonal to each other.

In both FIG. 8A and FIG. 8B, at least one minimum 76, 78, 80 is visible. Such minimum originates from the fact that the scattering signal originating from these positions of the fiber are not equally distributed over the detectors 32, 34 but correspond more closely to a 100-0 setting for the device branch. By a proper rotation as executed with the second setting of polarization controller 27 this unbalancing can be transformed to closely resembling a 50-50 splitting. This is depicted in FIG. 8B where the signals S1, S2, P1 and P2 have approximately the same amplitude at the fiber positions where in FIG. 8A they exhibit minima 76 and 78. At the same time the balancing of all the signals at the start of the fiber is maintained. The minimum 80 in FIG. 8B is recorded for a different position along the elongated fiber portion within the device 24 compared to the minima 76, 78 shown in FIG. 8A.

FIG. 8C shows four measurement traces S1', P1', S2', P2' which are obtained by combining the results from FIG. 8A and FIG. 8B. This means that each of the measurement traces S1', P1', S2', P2' is obtained by combining the two corresponding measurement traces detected by the same detector using the same input and output polarization setting in FIGS. 8A, B. It can be seen in FIG. 8C that the minima visible in FIGS. 8A, B are corrected, effectively correcting the effects of birefringence in the optical shape sensing system 10 and/or in the device 24. In particular, the lowest amplitude recorded in the measurement traces in FIG. 8C is increased by 12.8 dB compared to the lowest amplitudes shown in FIGS. 8A, B.

Preferably, the results of FIGS. 8A, B are combined using the signal analysis Method I or Method II and averaging the results of both methods with a weight factor which depends on the signal ratio of the two detectors.

Advantageously, the present optical shape sensing system 10, 10' enables to improve the birefringence correction, leading to increased SNR.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for sensing a shape of a medical device, comprising:
    an input polarization controller for setting an input polarization state of an input light signal,
    at least one interferometer unit for dividing input light signal into a medical device signal and a reference signal, guiding said device signal to be scattered within an optical fiber inserted into said medical device and coupling said scattered device signal with said reference signal to form an output light signal, and
    at least one measurement branch comprising an output polarization controller arrangement for setting an output polarization state of said output light signal, a polarizing beam splitter for splitting said output light signal into two signal portions, each being in a corresponding one of two signal portion polarization states, and a detector arrangement, comprising two detectors, each for detecting a corresponding one of said two signal portions, said input polarization controller being configured to set two pairs of input polarization states, or said output polarization controller arrangement is configured to set two output polarization states each for enabling a corresponding one of two pairs of signal portion polarization states, wherein: each pair of input or signal portion polarization states are representable by a corresponding one of two axes in a Poincaré sphere different from each other; and said input polarization controller is configured to set a reference polarization state of said reference signal, said reference polarization state corresponding to an eigen polarization mode of an optical fiber guiding said reference signal.

2. The system according to claim 1, wherein each pair of input or signal portion polarization states are representable by a corresponding one of two axes in a Poincaré sphere perpendicular to each other.

3. The system according to claim 1, wherein said two signal portion polarization states are orthogonal to each other.

4. The system according to claim 1, wherein each of said two pairs of input polarization states comprise two input polarization states orthogonal to each other.

5. The system according to claim 1, wherein said output light signal comprises two separate output signal parts, said output polarization controller arrangement being configured to set for each of said output signal parts a corresponding one of said two output polarization states.

6. The system according to claim 5, wherein said output polarization controller arrangement comprises two polarization controllers, each for setting one of said two output polarization states.

7. The system according to claim 5, wherein two polarization beam splitters and/or two detector arrangements are provided each for a corresponding one of said two output signal parts.

8. The system according to claim 1, wherein
    each pair of said signal portion polarization states are representable by two points on a surface of said Poincaré sphere defining a corresponding one of said two axes of said Poincaré sphere.

9. The system according to claim 1, wherein said two signal portions have equal signal amounts or one of said two signal portions has a signal amount essentially equal to zero.

10. The system according to claim 1, wherein said interferometer unit comprises a polarization controller for setting a polarization state of said medical device signal, said polarization controller) being arranged on an upstream signal side of said device.

11. The system according to claim 1, further comprising said optical fiber, said optical fiber comprising at least four cores each for separately guiding a corresponding one of at least four device signal parts of said device signal, and further comprising at least four interferometer units, wherein each core of said optical fiber is configured to cooperate with a corresponding interferometer unit and/or measurement branch.

12. A medical apparatus for optical shape sensing, comprising:
a medical device, and
the system as claimed in claim 1 for sensing a shape of said medical device.

13. A method for sensing a shape of a medical device, the method comprising:
setting an input polarization state of an input light signal;
dividing said input light signal into a device signal and a reference signal, guiding said device signal to be scattered within an optical fiber inserted into said medical device and coupling said scattered device signal with said reference signal to form an output light signal;
setting an output polarization state of an output light signal, splitting said output light signal into two signal portions, each being in a corresponding one of two signal portion polarization states, and detecting said two signal portions; and
setting a reference polarization state of said reference signal, said reference polarization state corresponding to an eigen polarization mode of an optical fiber guiding said reference signal, wherein said setting said input polarization state or said output polarization state comprises setting two pairs of input polarization states, or two output polarization states each for enabling a corresponding one of two pairs of signal portion polarization states, wherein each pair of input or signal portion polarization states are representable by a corresponding one of two axes in a Poincaré sphere different from each other.

14. A non-transitory computer readable medium having stored thereon instructions to control an apparatus, which, when being executed by a computer is adapted to perform the method of claim 13.

* * * * *